(12) United States Patent
Peyman et al.

(10) Patent No.: US 10,925,723 B2
(45) Date of Patent: Feb. 23, 2021

(54) OPTICAL IMPLANT AND METHODS OF IMPLANTATION

(71) Applicants: Gholam Peyman, Sun City, AZ (US); Lisa Brothers Arbisser, Sarasota, FL (US)

(72) Inventors: Gholam Peyman, Sun City, AZ (US); Lisa Brothers Arbisser, Sarasota, FL (US)

(*) Notice: Subject to any disclaimer, the term of this patent is extended or adjusted under 35 U.S.C. 154(b) by 0 days.

(21) Appl. No.: 16/827,106

(22) Filed: Mar. 23, 2020

(65) Prior Publication Data

US 2020/0237503 A1 Jul. 30, 2020

Related U.S. Application Data

(63) Continuation-in-part of application No. 16/140,801, filed on Sep. 25, 2018, now Pat. No. 10,660,743.

(51) Int. Cl.
*A61F 2/16* (2006.01)
*A61F 2/14* (2006.01)

(52) U.S. Cl.
CPC ............ *A61F 2/1694* (2013.01); *A61F 2/148* (2013.01); *A61F 2002/1681* (2013.01)

(58) Field of Classification Search
CPC .... A61F 2/1624; A61F 2/1627; A61F 2/1694; A61F 2/1605–1608
See application file for complete search history.

(56) References Cited

U.S. PATENT DOCUMENTS

| 4,596,578 | A | * | 6/1986 | Kelman | A61F 2/16 623/6.17 |
|---|---|---|---|---|---|
| 2008/0027537 | A1 | * | 1/2008 | Gerlach | A61L 27/50 623/6.22 |
| 2009/0021692 | A1 | * | 1/2009 | Miller | A61F 2/15 351/159.73 |
| 2011/0172649 | A1 | * | 7/2011 | Schuele | A61F 9/008 606/4 |
| 2016/0296662 | A1 | * | 10/2016 | Stoy | A61F 2/1627 |
| 2016/0374799 | A1 | * | 12/2016 | McCafferty | A61F 2/1651 623/6.34 |

* cited by examiner

*Primary Examiner* — Leslie Lopez
(74) *Attorney, Agent, or Firm* — Wood, Phillips, Katz, Clark & Mortimer

(57) ABSTRACT

An apparatus (200, 200A, 200B, 200C) has central lens body (212, 212A, 212B, 212C) for providing vision correction for a patient. The lens body (212, 212A, 212B, 212C) has an initial index of refraction and is formed from at least one material configured to have a second index of refraction when subjected to a laser and/or radiation.

13 Claims, 8 Drawing Sheets

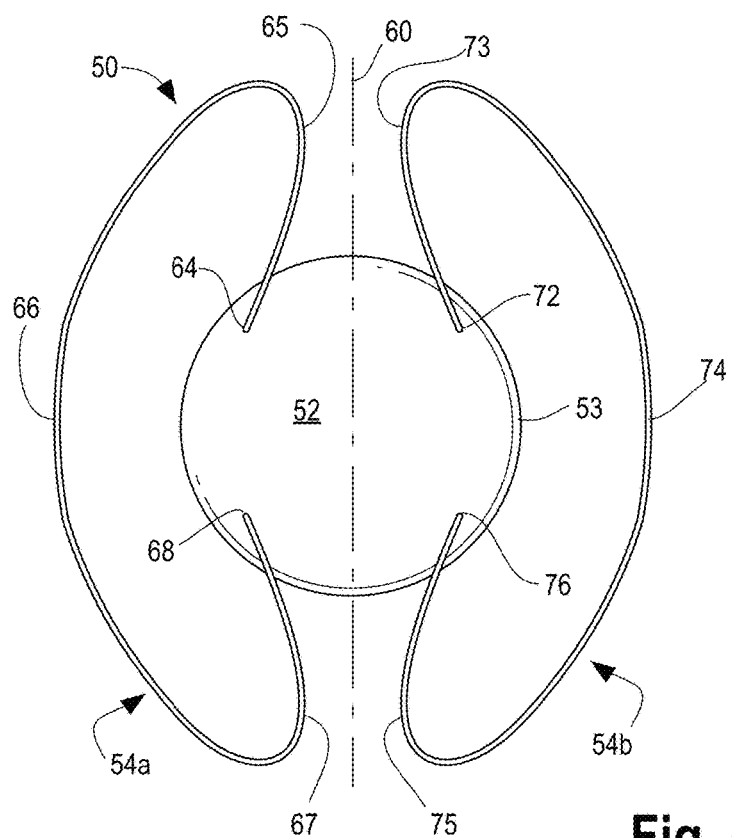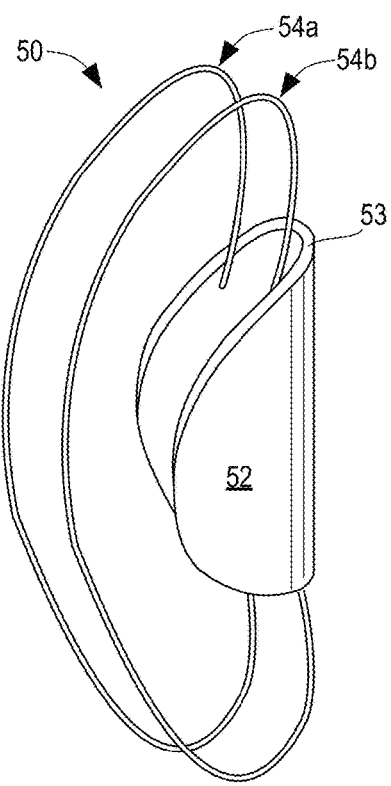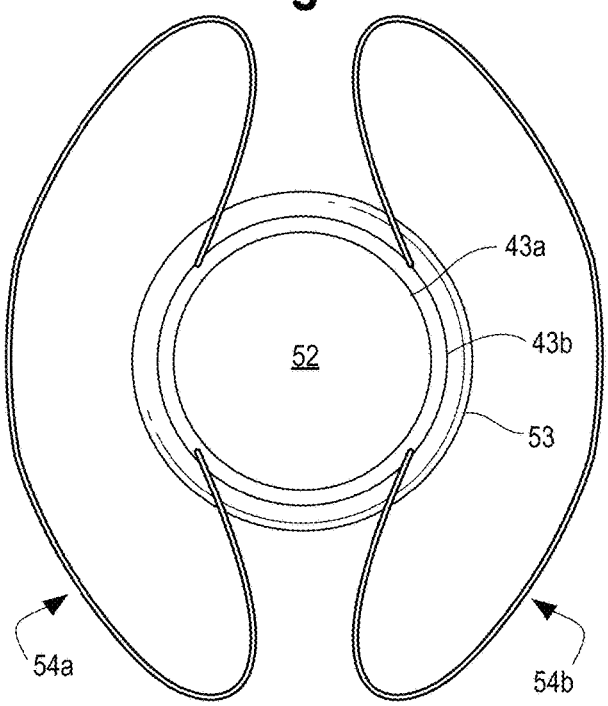

OPTICAL IMPLANT AND METHODS OF IMPLANTATION

FIELD OF THE INVENTION

The present invention relates generally to the field of ophthalmic surgery, and more particularly, to an improved intraocular lens, lens mate apparatus, and improved methods for implanting an intraocular lens and lens mate apparatus into a human or animal eye.

BACKGROUND OF THE INVENTION

Cataract is one of the most common causes of blindness. Approximately 20.5 million (17.2%) Americans have a cataract in either eye, and these numbers are rising. Cataract is most commonly seen between the ages of 45-64, with a lower prevalence in males than in females. Its symptoms are manifested by progressive cloudiness of crystalline lens of the eye, leading to glare, myopic shifts, monocular diplopia, and gradual loss of vision. The comorbidities are environmental conditions such as UV exposure, altitude, occupation, diet, smoking, alcohol, medication such as steroids and diseases such as ocular inflammation (uveitis) diabetes mellitus and hypertension, as side effects of x-ray radiation and in children traumatic eye injuries and genetic predisposition. The cataract is classified depending on the stage of the lens opacification as incipient, immature, and mature and hypermature, or the location of lens opacities as cortical, nuclear, posterior subcapsular.

The treatment for cataract is surgical removal of the involved lens and is achieved by various methods. It is done under a regional anesthesia, topical anesthesia, retrobulbar anesthesia and peribulbar anesthesia, etc.

One method of treatment is intracapsular cataract extraction ("ICCE") in which the entire lens including the lens capsule is removed in one piece. This requires a relatively large 7-10 mm corneal incision through which the lens is expressed out of the eye. The procedure is seldom performed because of its numerous complications of corneal keratopathy, vitreous loss, wound leak, iris incarceration, high astigmatism, post-operative inflammation, cystoid macular edema, retinal detachment and high rate of the infection and corneal complications (bullous keratopathy). Following the operation, patients have been prescribed thick refractive glasses, which may be difficult to maintain on the patient's nose. The patients of this operation have been prone to falling when going down the stairs, and fractured bones were not an uncommon problem in these patients, even increasing the patient's mortality.

Another method of cataract treatment is extracapsular cataract extraction ("ECCE"), a procedure in which the lens cortex and nucleus is removed by an aspiration and irrigation system after removal of a part of the anterior capsule, while the rest of the capsule remains in place. This procedure has been performed most often in children having congenital cataract to avoid disrupting the posterior capsule to prevent vitreous loss. The surgery has been associated with serious post inflammatory response, glaucoma, proliferation of lens epithelial cells producing severe capsular opacification and fibrosis, and potentially retinal detachment when the posterior capsule has been inadvertently violated.

Yet another method of cataract treatment is extracapsular cataract extraction with phacoemulsification combined with intracapsular implantation of an acrylic intraocular lens ("IOL"). In this procedure, the lens cortex and nucleus are removed through a relatively small corneal incision, between about 4 mm to 5 mm in diameter, and an anterior capsulotomy. Then, an ultrasonically driven needle is used to emulsify the lens cortex and nucleus, which are then removed by an irrigation/aspiration of fluid and the lens cortical material. Subsequently, a folded IOL is implanted inside the lens capsule through a small corneal incision. While this concept has brought significant improvement to the technique of cataract surgery and benefit for the patient, the remaining lens epithelial cells have been found to attach to the anterior capsule, often proliferating posteriorly to produce a posterior capsular cloudiness and fibrosis which reduces post-operative visual acuity in the patient. Treatment of this complication involves either an yttrium aluminum garnet ("YAG") laser capsulotomy, or the removal of the part of the posterior capsule with a vitrectomy instrument by cutting and removing central part of the posterior capsule and the vitreous in order to clear the optical media. This procedure has been done routinely in the developed countries, however, it is not easily done in developing countries with a large cataract population because of the cost of a YAG-laser and/or the difficulty for the patient to return to a surgery center for an additional surgery.

An alternative procedure is to perform a limited central anterior and posterior capsulotomy in a single procedure, and the lens optic is implanted in the space of Berger located between the posterior lens capsule and anterior hyaloid membrane, while the lens haptics remain substantially in front of the lens capsule located in the posterior chamber contacting the ciliary body. When done properly, this procedure leaves a clear optical media in one surgical session without the need for subsequent need for the posterior capsulotomy. The lens capsule folds upon itself in this procedure.

In general, IOL implantation has a decades long history of biocompatibility in the eye. The IOLs are made from polymeric materials such as PMMA, silicone, hydrogel, polyvinylidene fluoride, or in combination with collagen as Collamer, multifocal IOLs are effective in providing near and far vision after cataract surgery. Toric IOLs are used to correct corneal astigmatism, such as the Alcon acrylic toric IOLs or the Johnson and Johnson Tecnis Toric 1-piece IOL.

Despite the advances in cataract surgery and the construction of the new IOLs, there are still some problems the patients have to deal with, that affect their visual satisfaction in the post-operative period.

For example, the IOLs can tilt either in a horizontal or vertical direction inducing great dissatisfaction for the patient. This happens frequently if the capsulotomy is not done properly or the lens zonulas are genetically affected in diseases such as in patients with Marfan syndrome, Morgagnian cataract, high myopia, or after traumatic injuries where the zonulas can become weak or broken, and the incomplete or partial lens zonulae contribute to a tilted IOL.

The IOLs can tilt or settle in the post-operative period as a result of capsular fibrosis after cataract surgery, for example, if the haptic and optics are inside the capsular bag and an uneven pressure is generated as a result of capsular fibrosis or a large capsulotomy.

IOLs seldom have a perfect refractive power to create an emmetropic refraction after surgery. In majority of cases the IOLs refractive power is off by plus or minus 0.5 D power or more, which is not easy to correct if the IOLs are multifocal lenses.

Lens centration is very important for multifocal lenses, otherwise patients are not satisfied with their vision and a lens exchange may be needed.

Children's eyes and myopic eyes grow significantly, requiring removal of the IOL and their replacement.

Capsular opacification occurs after the cataract surgery when the lens epithelial cells, located behind the anterior capsule, start proliferating inside the lens capsule to fill the empty space left inside the capsule after cataract extraction while the post-operative inflammatory response persists.

One prior art method for replacing the accommodative power of the crystalline lens has been to implant a prior art multifocal IOL. However, such lenses have had shortcomings in that if they were not perfectly corrected for far vision, the rest of the prior art multifocal IOL zones would not be perfectly corrected either. Further, the prior art multifocal IOL has been prone to de-centration issue or double vision.

A need remains for a patient to have only a single operation to correct the patient's vision over the lifetime of the patient, even for patients that are infants or minors.

SUMMARY OF THE INVENTION

The inventor of the present invention has discovered an improved intraocular lens construction for implantation into an eye and novel methods for implanting the improved intraocular lens within the eye.

According to one form of the present invention, an apparatus or lens mate is provided for being locate anterior of an existing intraocular lens or natural lens. The lens mate includes a lens body for providing vision correction for a patient and has an initial index of refraction. The lens body is formed from at least one material configured to have a second index of refraction when subjected to a laser and/or radiation.

In one form of the present invention, the lens body has the form of a substantially flat disc.

According to another form of the present invention, the lens body has a central aperture. In one preferred form, the lens body is formed from a substantially transparent material and the central aperture includes a darkened perimeter. In still another preferred form, the central aperture has the form of an elongate slot or circular hole.

In still another form of the present invention, the lens mate includes one or more stabilizing haptics extending from the lens body.

In one form of the present invention, lens mate further includes at least one peripheral slot extending laterally inwardly from a peripheral portion of the lens body for engaging a haptic of an intraocular lens located beneath (superior) to the lens mate.

According to one aspect of the present invention, the lens mate is provided in combination with an intraocular lens and is arranged such that the lens mate overlies and is anterior of the intraocular lens when implanted in the eye.

According to yet another aspect of the present invention, the lens body is formed from a photosensitive material and may optionally include a layer of a photosensitizer.

In another form of the present invention, a first portion of the lens body is formed from a first polymer and a second portion of the lens body is formed from a second polymer, whereby the second polymer is softer than the first polymer.

According to yet another aspect of the present invention, the lens body includes one or more zones surrounding the central aperture which have an index of refraction that is different from that of a remaining portion of the lens body.

According to one form of the present invention, a method of implanting the lens mate in an eye includes the steps of obtaining and implanting the lens mate in the eye and applying a femtosecond laser to the lens body to change its initial index of refraction in situ.

Other features and advantages of the present invention will become readily apparent from the following detailed description, the accompanying drawings, and the appended claims.

BRIEF DESCRIPTION OF THE DRAWINGS

FIG. 3 is an enlarged, top plan view of an embodiment of an improved intraocular lens according to the present invention;

FIG. 4 is an enlarged, perspective view of the intraocular lens shown in FIG. 3 in a folded configuration prior to being implanted within the human eye;

FIG. 5 is an enlarged, top plan diagrammatic view of the intraocular lens shown in FIG. 3 implanted within the human eye, and FIG. 5 shows the central lens body tucked behind the anterior and posterior capsule and the lens haptics located overtop of the anterior and posterior capsule;

FIG. 6 shows the central lens body tucked behind the anterior and posterior capsule and the lens haptics located overtop of the anterior and posterior capsule;

FIG. 7 shows the central lens body located overtop of the anterior and posterior capsule and the lens haptics tucked behind the anterior and posterior capsule;

FIG. 8 illustrates the location of the lens body relative to the lens capsule in the first configuration of FIG. 6 (solid line) and further illustrates the location of the lens body relative to the lens capsule in the alternative configuration of FIG. 7 (phantom line);

FIG. 12 shows the lens mate mechanically engaging the haptics of the intraocular lens.

DETAILED DESCRIPTION OF THE PREFERRED EMBODIMENTS

Figure 1:
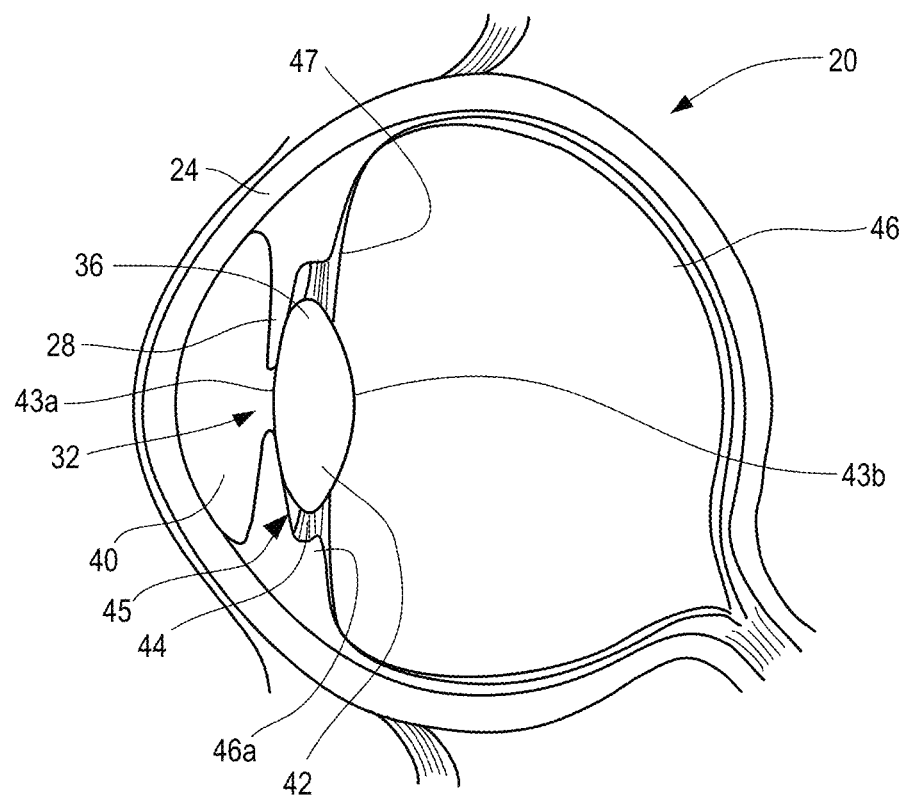
FIG. 1 is an enlarged, diagrammatic view of a human eye

While the present invention is susceptible of embodiment in various forms, there is shown in the drawings and will hereinafter be described a presently preferred embodiment of the invention, with the understanding that the present disclosure is to be considered an exemplification of the invention, and is not intended to limit the invention to the specific embodiment illustrated.

Figure 2:
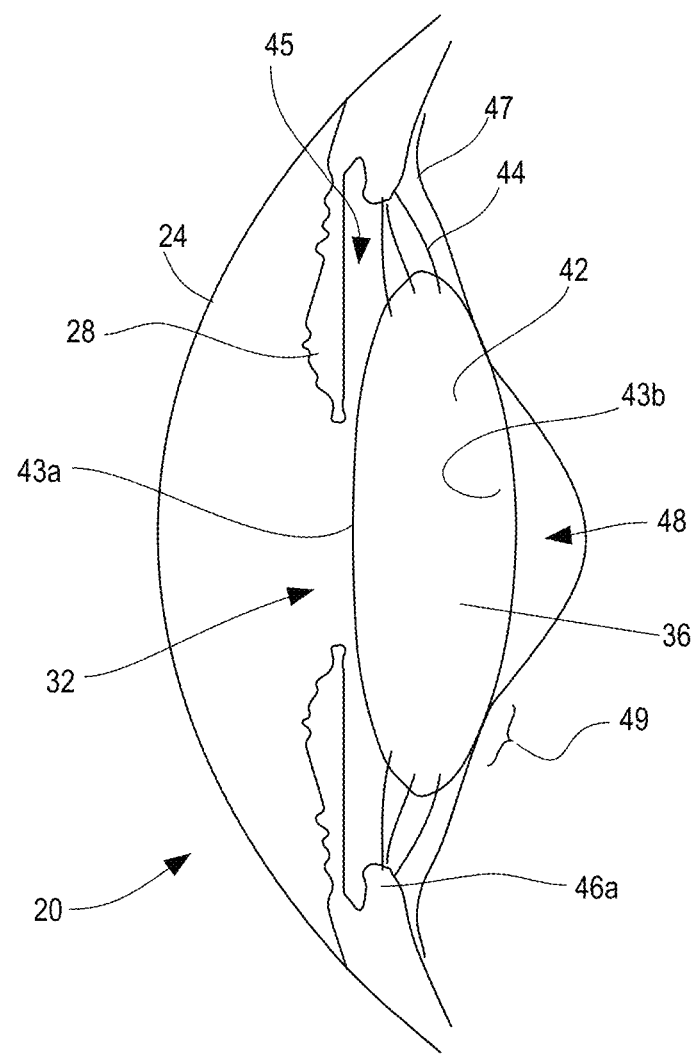
FIG. 2 is a greatly enlarged, diagrammatic view of the anterior segment of the human eye.

FIGS. 1 and 2 show a diagrammatic view of the human eye 20. Beginning at the exterior of the eye 20, the eye 20 has a protective outer layer or cornea 24 which retains the fluids or aqueous humor of the eye 20 and which focuses light. Inward of the cornea 24 is the ring-like iris 28 with an aperture or pupil 32 for restricting light reaching the lens 36. The lens 36 defines the posterior extent of the anterior segment 40 of the eye 20, sitting behind the iris 28. The lens 36 is composed of protein encased in a capsular bag 42. Supporting ligaments or zonules 44, composed of 360 degrees of attachments anterior, equatorial, and posterior, and together with Wieger's ligament (49 in FIG. 2) which defines the space of Berger (48 in FIG. 2), stabilize and center the capsular bag 42 within the eye 20. Opposing the anterior segment 40 of the eye 20 is the posterior segment 46 containing the vitreous body, optic nerves, veins, and arteries of the eye 20. The capsular bag 42 has a forward or anterior wall or portion 43a and a rearward or posterior wall or portion 44b that together retain the denser, hard lens nucleus and the surrounding, less dense lens cortex. A crevice or sulcus 45 exists between the iris 28 and the ciliary body 46a. The anterior hyaloid membrane 47 is located behind the capsular bag 42 and separates the vitreous humor of the eye from the anterior segment 40.

Figure 6:
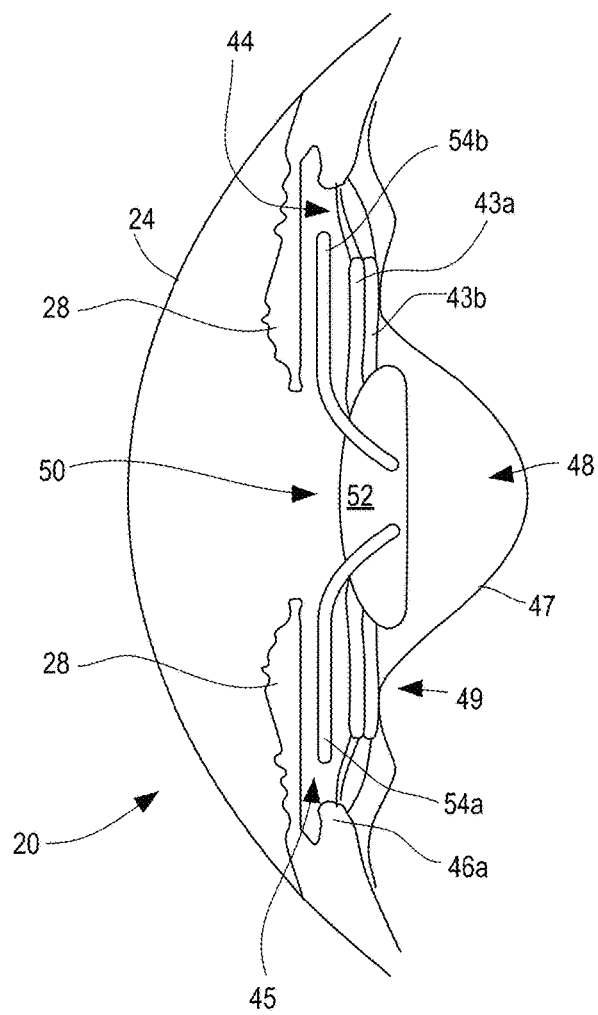
FIG. 6 is an enlarged, side elevation diagrammatic view of the intraocular lens shown in FIG. 3 implanted within the human eye.
Figure 7:
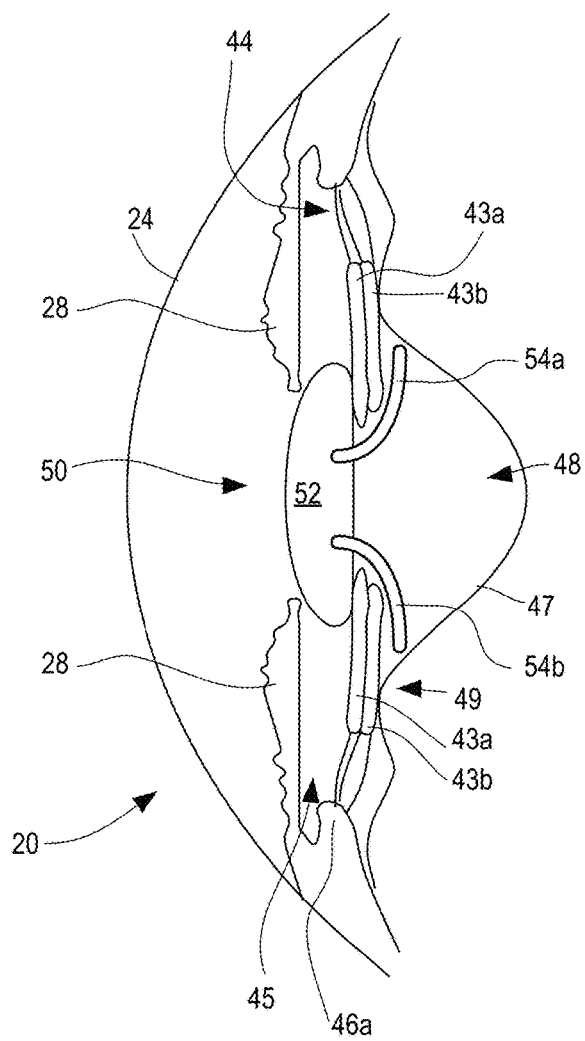
FIG. 7 is an enlarged, side elevation diagrammatic view of the intraocular lens shown in FIG. 3 implanted in an alternative configuration within the human eye.
Figure 8:
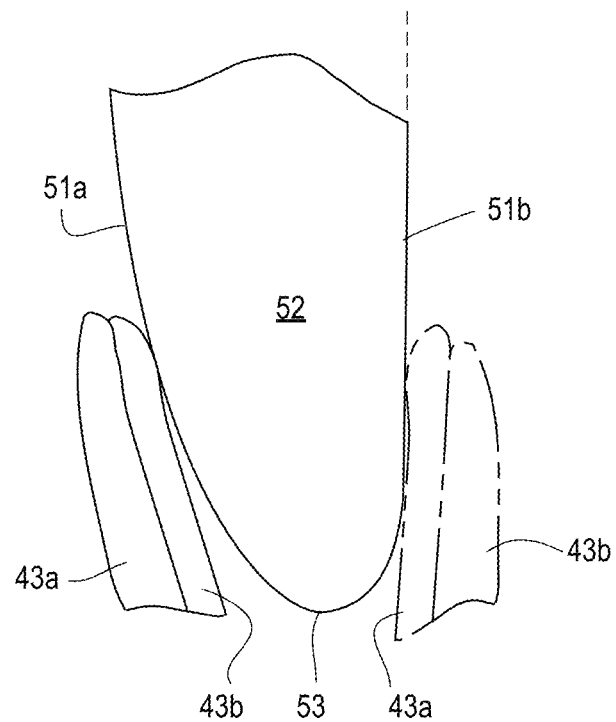
FIG. 8 is a greatly enlarged, detailed side elevation diagrammatic view of the engagement of the intraocular lens shown in FIG. 3 with the lens capsule.

As will be discussed in greater detail hereinafter, the inventors have developed advantageous methods for the prevention or minimization of the likelihood of proliferation of lens epithelial cells after the ECCE procedure discussed above. In one preferred method, a bio-compatible adhesive, such as FDA-approved synthetic polyethylene glycol hydrogel sealant sold under the trade name ReSure Sealant by Ocular Therapeutix, Inc. of Bedford Mass., is injected into the capsule after ECCE to seal the emptied anterior capsular portion 43a and posterior capsular portion 43b tight (hereinafter, the sealed portions 43a and 43b, which are illustrated in FIGS. 6-8, may collectively be referred to as "leaflets"), so that substantially no free space remains within the capsular bag 42 where aqueous and inflammatory cytokines may ingress and stimulate cell proliferation. The injection of bio-adhesives along with an anti-inflammatory agent, such as dexamethasone at low concentration of about 100 micrograms-400 micrograms per 0.05 milliliter ml or more, or in combination with an antibiotic may be done using a small 27 gauge needle either before or after IOL implantation to slowly release the medication and prevent separation of the capsular bag leaflets after the surgery and to prevent inflammation and/or infection and the growth of the anterior lens epithelial cells inside the capsule.

The bio-compatible tissue adhesive that is injected inside the leaflets 43a and 43b may require ultraviolet radiation to permanently close or seal the space between the leaflets 43a and 43b to prevent lens epithelial cell proliferation and capsular opacification. The tissue adhesive can be made to of absorbable or non-absorbable polymers. Preferably, the biocompatible adhesive does not induce any refractive change of the IOL that is implanted subsequent to the sealing of the leaflets 43a and 43b, and the adhesive is spaced or separated completely from the IOL.

The inventors believe that sealed lens capsule leaflet (43a and 43b) may hold an IOL tight to provide a better forward and backward motion of the lens capsule and IOL, as compared to the prior art ECCE implantation methods, during the accommodation or contraction of the ciliary body muscles for seeing near objects or far objects as would happen with the normal, healthy eye.

FIGS. 3-8 show one preferred, improved intraocular lens (IOL) 50 embodying the principles of the present invention. Attendant to a phacoemulsification procedure for removal of the natural lens nucleus and cortex from the capsular bag 42, the IOL 50 is especially suited for the implantation techniques that will be discussed in detail hereinafter. The lens 50 has a central lens body or optic 52 made from a biocompatible transparent polymeric material such as PMMA, silicone, hydrogel, or acrylic, and portions of which may be hydrophobic, hydrophilic, or amphiphilic, or a combination thereof.

With reference now to FIG. 8, the central lens body 52 has a first and second, opposite anterior (anterior with respect to the frontal plane) and posterior (posterior with respect to the frontal plane) surfaces 51a and 51b, respectively. The posterior surface 51b of the lens body 52 generally resides in a plane 55. The central lens body 52 has a suitable cross-sectional configuration for providing vision correction for the patient, which is known in the art. The anterior surface 51a and posterior surface 51b of the central lens body 52 meet or join in a rounded peripheral or side surface 53. As will be discussed in detail hereinafter, one or more of the surfaces of the lens body 52 are especially suited for engaging the sealed leaflets 43a and 43b of the capsular bag 42. To this end, one or more of the surfaces 51a, 51b, and/or 53 may be treated with a surface treatment or applied layer of a different material, or made from a material that is different from the remaining portion of the lens body 52, to enhance sealing of the lens body 52 with the sealed leaflets 43a and 43b.

The lens body 52 may have one or more surfaces of a varying degree of convexity depending on the need for correction to the patient's vision. The lens body 52 may have a toric or spherical shape, a positive dioptric power, or possess multiple focal points to correct a patient's vision as is known in the art.

Referring to FIG. 3, the lens 50 further preferably includes a pair of haptics 54a and 54b extending from the central lens body 52 in a bi-lobular or "butterfly" configuration that surrounds the circular optic in a semi-oval fashion creating two wings that connect the superior portion of the lens body 52 to its inferior part. The haptics 53a and 54b are inserted or connected to the lens body 52 in either (i) a parallel fashion with respect to the plane of the posterior surface 51b of the lens body 52, or (ii) an angled or offset fashion with respect to the plane 55 defined by the posterior surface 51b of the lens body 52, producing a slight separation or angle between the plane 55 of the posterior surface 51b of the lens body 52 and attachment points of the haptics 54a and 54b, whereby the leaflets 43a and 43b of the lens capsule 42 may sit comfortably against the lens 50 and contribute to the closure of the space between the anterior and the posterior capsule (FIG. 6 or 7) to prevent or at least minimize the likelihood of capsular opacification, tilt and provide balance and stability to the IOL 50 within the eye.

With reference to FIG. 3, the haptics 54a and 54b are generally symmetric about a central axis 60 of the IOL 50. The path of the haptic 54a, which is generally kidney shaped, includes a first point of connection 64 to the lens body 52 and extends toward the central axis 60 before curving back away from the central axis 60 at a first distal end 65. From the first distal end 65, the haptic 54a extends away from the central axis 60 in an arc toward a medial point 66, at which point the haptic 54a curves back toward the central axis 60. The haptic 54*a* includes a second distal end 67 where the haptic 54*a* curves back away from the central axis 60 to a second point of connection 68.

Still referring to FIG. 3, the path of the haptic 54*b* includes a first point of connection 72 to the lens body 52 and extends toward the central axis 60 before curving back away from the central axis 60 at a first distal end 73. From the first distal end 73, the haptic 54*b* extends away from the central axis 60 in an arc toward a medial point 74, at which point the haptic 54*b* curves back toward the central axis 60. The haptic 54*b* includes a second distal end 75 where the haptic 54*b* curves back away from the central axis 60 to a second point of connection 76.

As will be discussed below, the haptics 54*a* and 54*b* have a configuration that may be advantageously engageable with the ciliary body 46*a* for stabilizing the lens 50 (FIG. 6). Alternatively, the haptics 54*a* and 54*b* may be located behind the leaflets 43*a* and 43*b* for stabilizing the lens 50 (FIG. 7).

With reference to FIG. 4, the lens 50 would be implanted using standard or customized injectable technology by folding it and injecting it in the desired location within the eye along with a viscoelastic material through a very small incision in the cornea 24. The viscoelastics would then be washed away with saline solution after implantation to prevent rise in the intraocular pressure.

With reference now to FIG. 6, in one preferred configuration of implantation of the IOL 50, the lens body 52 or optic is positioned in the space of Berger 48, such that the leaflets 43*a* and 43*b* lie overtop of the lens body 52. In this configuration, the haptics 54*a* and 54*b* lie substantially (e.g., almost entirely) over the anterior capsule 43*a*, and may lie on the zonulas 44 (if intact), or may reach the ciliary body 46*a* to make the IOL 50 independent from the lens capsule 42 in case the weak or ruptured zonulas 44. The haptics 54*a* and 54*b* may reach or touch the sulcus 45 between the ciliary body 46*a* and the iris 28 (not illustrated). Contact between the haptics 54*a* and 54*b* with the ciliary body 46*a* is also limited to two points on each side of the lens body 52 to limit the undesirable uncontrolled penetration of the lens haptic 54*a* and 54*b* inside the ciliary body 46*a*, which could cause bleeding or irritation or inflammation in the eye. The inventors believe that the configuration of the bi-lobe haptics 54*a* and 54*b* may provide a better-balanced lens optic or lens body 52 and create a better centration for the lens body 52 to prevent or minimize the likelihood of tilting of the IOL 50.

With reference now to FIG. 7, in one alternative configuration of implantation of the IOL 50, the lens body 52 or optic is positioned behind the iris 28 such that it lies overtop of the leaflets 43*a* and 43*b* to balance the lens optic or lens body 52 and create a better centration for the lens body 52 to prevent or minimize the likelihood of tilting of the IOL 50.

The inventors believe that in the IOL 50 implantation configuration illustrated in FIGS. 5, 6, 7, and 8, the lens body 52 or optic acts like a plug to close the opening in the posterior or anterior chamber preventing penetration of the vitreous into the anterior chamber, which would have undesirable complications.

In an alternative configuration, not illustrated, the IOL 50 is implanted such that lens body 52 is located in an intermediate position, within the lens capsule 42.

The inventors of the present invention believe that the IOL 50 and the methods of implantation described above may be beneficial to prevent or at least minimize the likelihood of secondary cataract of the posterior portion 43*b* of the lens capsule 42 such that duplicative or remedial surgeries, common with prior art surgical procedures and lens designs, may be minimized or eliminated over the lifetime of the patient.

In another embodiment, the IOL 50 can act as an additional, or secondary IOL to a normal crystalline lens to correct either a high myopic eye In another embodiment, the IOL 50 can be positioned over an existing IOL in a previously operated upon eye to compensate for the existing refractive errors of the eye eliminating the need for a complex surgery of removing an existing IOL from its capsular bag and eliminating or reducing post-operative trauma contributing to a faster visual rehabilitation and wound healing.

Figure 9:
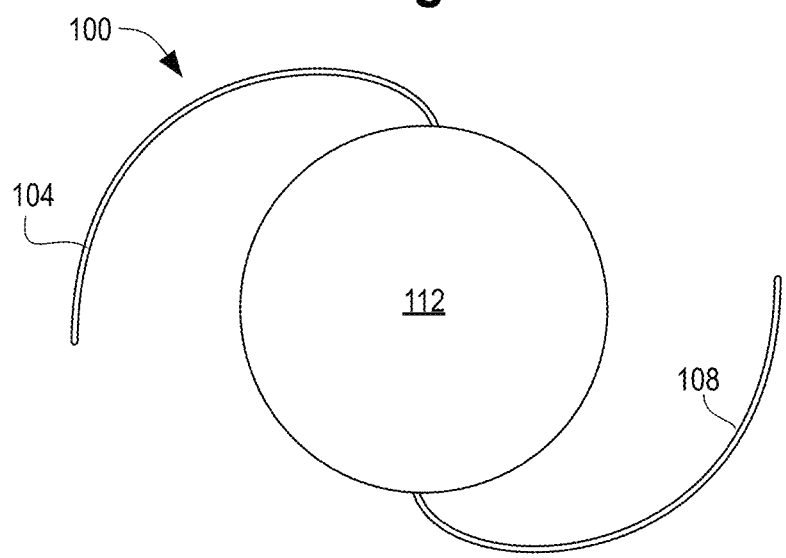
FIG. 9 illustrates a top plan view of a secondary intraocular lens that may be implanted overtop of the intraocular lens shown in FIG. 3.

In one embodiment, the surgical methods disclosed herein may be modified for younger patients, adults or children, in whom the eye grows and requires a different refractive correction over time. In such a modified method, a secondary IOL such as the IOL 100 illustrated in FIG. 9 is implanted over, e.g., in front of, the initially implanted intraocular lens 50. The secondary IOL 100 includes a pair of haptics 104 and 108 which have discrete endpoints or poles, and which are not in the form of loops. The secondary IOL 100 further includes an optic or lens body 112, which may be a plus, a minus or a toric IOL depending on the patient's need. The secondary IOL 100 is preferably implanted with its haptics 104 and 108 positioned generally 90 degrees relative to the haptics 54*a* and 54*b* of the inventive IOL 50 (e.g., generally extending perpendicular to the central axis 60) such that the haptics 104 and 108 are located over the existing crystalline lens or zonulae 44 in the posterior chamber behind the iris 28. The secondary IOL 100 and the IOL 50 are separated or spaced from each other at all times.

The secondary IOL 100 is generally self-maintained in the eye due to the structure of its haptics 104 and 108 and the structure of the eye, and the secondary IOL 100 does not adhere to the lens capsule 42. Thus, the secondary IOL 100 can be easily removed or replaced without tearing or cutting the tissue of the eye.

The stacked positions of these two IOLS 50 and 100 might have an implication in creating an accommodative lens where the lenses get closer to each other and separate from each other depending on the accommodative process and contraction of the ciliary muscles and their pull on the lens, zonulas/capsule puling it forward or relaxing it backward.

In another embodiment of the present invention, one can modify the index of refraction of the IOL 50 or 100 non-invasively by changing its index of refraction using a femtosecond laser as needed throughout the patient's life. In some applications, the IOL 50 or 100 has a fixed refractive power. However, the refractive index of the IOL 50 or 100 can be modified to create bifocal, trifocal, multifocal or toric lens prior to the surgery or afterward using nanojoule pulses of a femtosecond laser applied to the surface of the IOL 50 or 100. The IOL 50 or 100 may be provided with an extra soft polymeric surface such as crosslinked collagen. The inventors believe that such a lens would prevent or at least minimize the likelihood of the problems associated with multi focal lenses which include, tilt, capsular opacification, off-axis positioning and the difficulty of lens exchange.

In one form, the surface of the IOL 50 or 100 is exposed to low energy nanojoule femtosecond pulses to modify the index or the refraction of the lens 112 to the desired power and the control of a wave front technology unit to accurately provide accurate femtosecond pulses to the lens surface and create an emmetropic refraction or multifocal refraction as desired for the patients' need.

Figure 10:
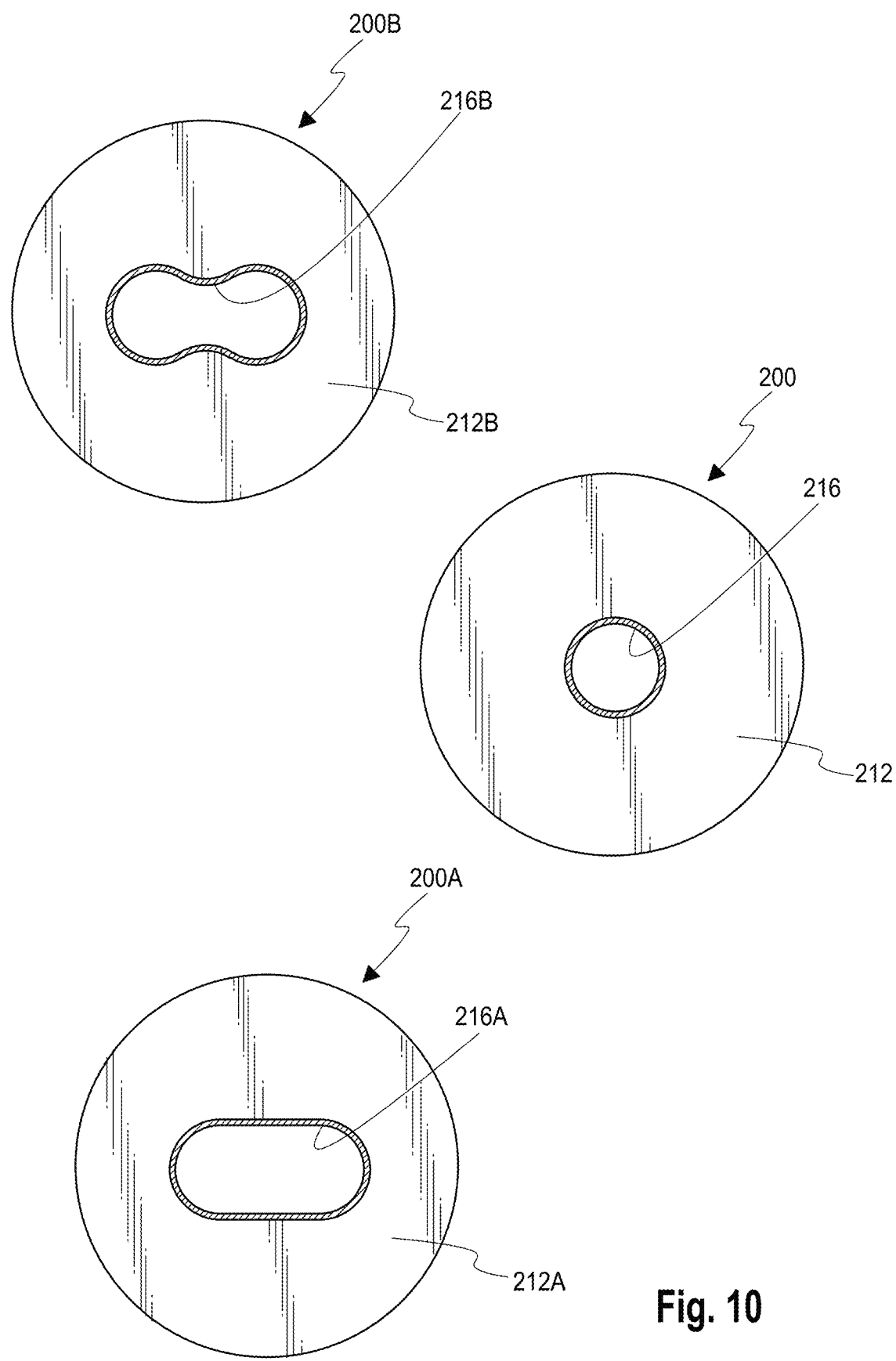
FIG. 10 illustrates a top plan view of three different embodiments of a lens mate or secondary body that may be implanted overtop (anterior) of an intraocular lens, such as that shown in FIG. 3, whereby the refractive power of the lens mate may be modified in situ using a laser.

Referring now to FIG. 10 a secondary body may be provided in the form lens mate 200, which is a substantially flat plate or disc, oval, or thin cylinder, for being implanted over, i.e., in front of, or anterior to, an implanted intraocular lens, such as the aforementioned lens 50 or a commercially available prior art IOL. The first illustrated embodiment of the lens mate 200 includes an optic or lens body 212 that is free of any haptics, and which preferably has no correction (i.e., is optically neutral) at the time that the lens mate 200 is implanted in the eye. The body 212 is preferably between 4.0-8.0 mm in diameter with a thickness (out of the plane of view in FIG. 10) of between about 0.05 mm and 3.0 mm. The lens body 212 includes a central hole or aperture 216 that may be between about 1.0 and about 3.0 mm in diameter. The aperture 216 is surrounded by a darkened portion of the lens body 212 or wall along its perimeter to prevent or minimize light scattering, and rendering a pin hole effect to the light by extending the focal point area for the near objects and focusing on the distant objects for a patient.

Figure 13:
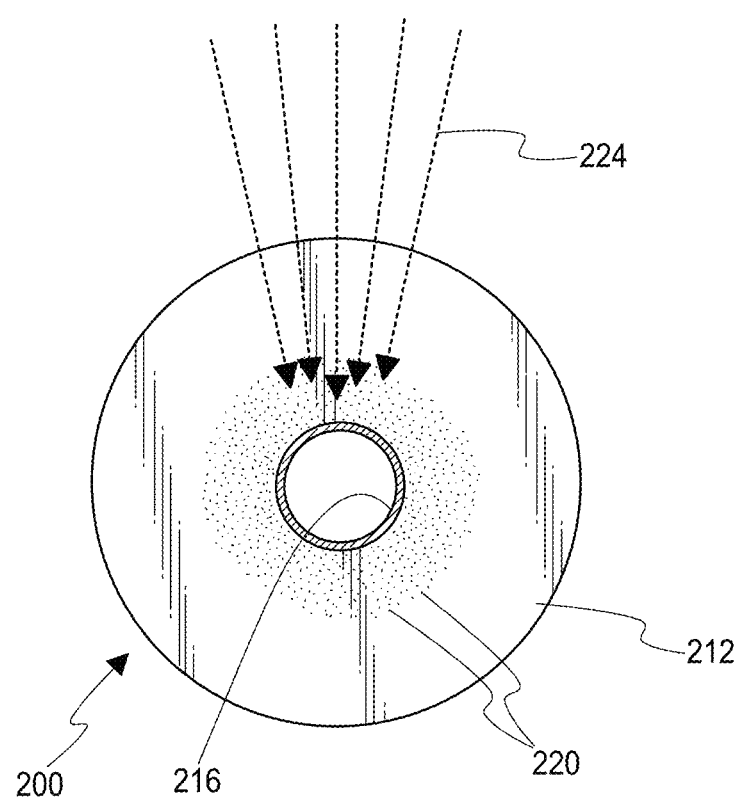
FIG. 13 illustrates a diagrammatic top plan view of one of the three different embodiments of the lens mate shown in FIG. 10 being subjected to a femtosecond laser to modify its refractive power in a zone around a central aperture subsequent to implantation in the eye.

The lens mate 200 is preferably formed from one or more semi-flexible, flexible, or foldable transparent polymeric materials such as PMMA, acrylic, silicone, hydrogel, or combination of silicone hydrogel or crosslinked collagen or elastin, etc. such that the body 212 index of refraction may be modified non-invasively by using a femtosecond laser as needed throughout the patient's life. In some applications, the lens mate 200 has a fixed refractive power. However, the refractive index of the lens mate 200 preferably can be modified to create bifocal, trifocal, multifocal or toric lens prior to the surgery or afterward using nanojoule pulses of a femtosecond laser applied to the surface of the body 212 as will be discussed in greater detail below. The body 212 may be provided with an extra soft polymeric surface such as crosslinked collagen. The inventors believe that such a lens mate 200 would prevent or at least minimize the likelihood of the problems associated with multi focal lenses which include, tilt, capsular opacification, off-axis positioning and the difficulty of lens exchange. The refractive power of the lens body 212 is corrected as needed, prior to implantation or in the post-operative period by femtosecond laser pulses 224, as shown in FIG. 13, to create zones or regions 220 of modified refractive index for near and/or intermediate vision correction. The degree of the correction needed may be measured initially, and input into an algorithm of the software or application controlling the laser output to achieve the desired refractive change in the lens mate 200.

In some applications, multiple zones around the central aperture 216 can be created to produce a multifocal zone around the central area of the body 212 using the femtosecond laser application with desired spot size power, and frequency under automated scanning OCT for precise localization of laser application and its extent using the laser's software. The refractive error of the eye, such as astigmatism, defocus, coma, etc. may be corrected with the laser acting upon the body 212 of the mate 200 in the postoperative period. In one form, the changes in the index of refraction of the body 212 of the mate 200 is measured by a shack-Hartmann system during the surgery.

In one method, the surface of the body 212 may be exposed to low energy nanojoule femtosecond pulses to modify the index or the refraction of the lens body 212 to the desired power and the control of a wave front technology unit to accurately provide accurate femtosecond pulses to the lens surface and create an emmetropic refraction or multifocal refraction as desired for the patient's need. In one application, prior to the implantation in the patient, the polymeric lens body 212 may be dipped in a 0.1% riboflavin or other non-toxic photosensitizers preparation to penetrate the soft polymeric plate to enhance refractive index modification or make the body 212 suitable for refractive index modification with a femtosecond laser. Alternatively, 0.05 ml riboflavin or other suitable photosensitizer agents at 0.1% concentration can be injected with a 32-34 gauge needle in the anterior chamber prior to modification of the lens mate's index of refraction during the surgery or in the postoperative period using a femtosecond laser.

In one presently preferred method, the surface of the lens body 212 may be irradiated with a femtosecond laser with a wavelength of 300 nm to 1000 nm or 350 nm-700 nm or 700 nm to 1300 nm and the energy level of 0.05 nJ to 1000 nJ or more to change the index of the refraction around the central aperture 216 rendering these areas with a higher index of refraction enhancing the reading ability combined with the increased depth of the focal or the pinhole of the transparent flexible mate 200. Alternatively, the of the lens body 212 polymer may be subjected to irradiation to induce changes in its index refraction around the central aperture 216.

In one preferred application, the femtosecond pulse frequency is preferably between 1 MHz to 10 MHz or between 500 MHz to 1 GHz with a pulse length of 10 femtoseconds to 1000 femtoseconds.

In another application, the femtosecond pulse energy may range between about 0.2 nJ and about 15 nJ or greater and the focal point may be between about 0.3 micrometer and about 2 micrometers or greater. Preferably, the laser pulses scan at a speed of between about 10 mm/s to about 1000 mm/s.

Referring to FIG. 10, it will be understood that the aperture 216 in the lens mate 200 may be modified and need not be circular. For example, a lens mate 200A may be provided with a body 212A having an aperture 216A in the form of an oval or elongate slot surrounded by a darkened wall or portion of the body 212A along its perimeter. In still another form of the present invention, a lens mate 200B may be provided with a body 212B having an aperture 216B in the form of a dumbbell or infinity shape surrounded by a darkened wall or portion of the body 212B along its perimeter.

Figure 11:
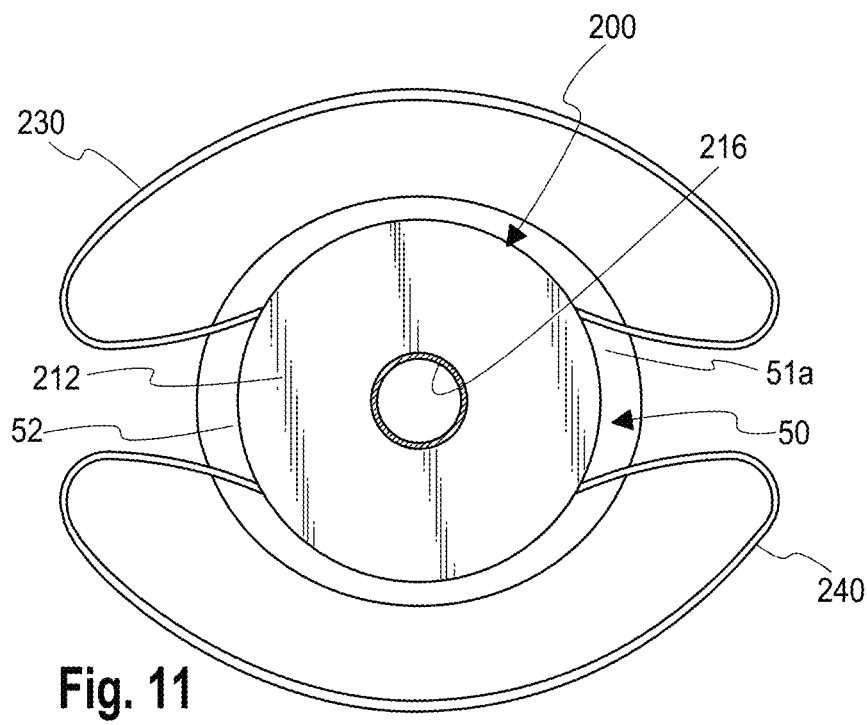
FIG. 11 illustrates a top plan view of one of the three different embodiments of the lens mate shown in FIG. 10 implanted overtop (anterior) of the intraocular lens of FIG. 3, and the lens mate of FIG. 11 is provided with its own haptics for stabilization within the eye.

Referring to FIG. 11, in another form of the present invention, the lens mate 200 may be provided with one or more of its own haptics 230/240 that reach the ciliary body for fixation. The haptics 230/240 of the lens mate 200 are preferably kidney-shaped, closed loops. It will be understood that the haptics 230/240 may have other shapes, such as the haptics 51a and 51b of the IOL 50, or may be cantilevered arms that are not in form of loops.

The inventors of the present invention intend that the lens mate 200 and the primary IOL may mounted and then implanted in the eye with viscoelastic fluid such as hyaluronic acid through an injector. Alternatively, the IOL may be implanted first, followed by the separate implantation of the lens mate 200 by way of a plunger type injector, as is known in the art. The lens mate 200 and the primary IOL, such as the IOL 50 or any prior art IOL, may be connected or spaced from each other at all times. The lens mate 200 is designed to be easily removed or replaced as needed in the postoperative period through a sub-2 mm incision under topical anesthesia under a slit-lamp observation.

Figure 12:
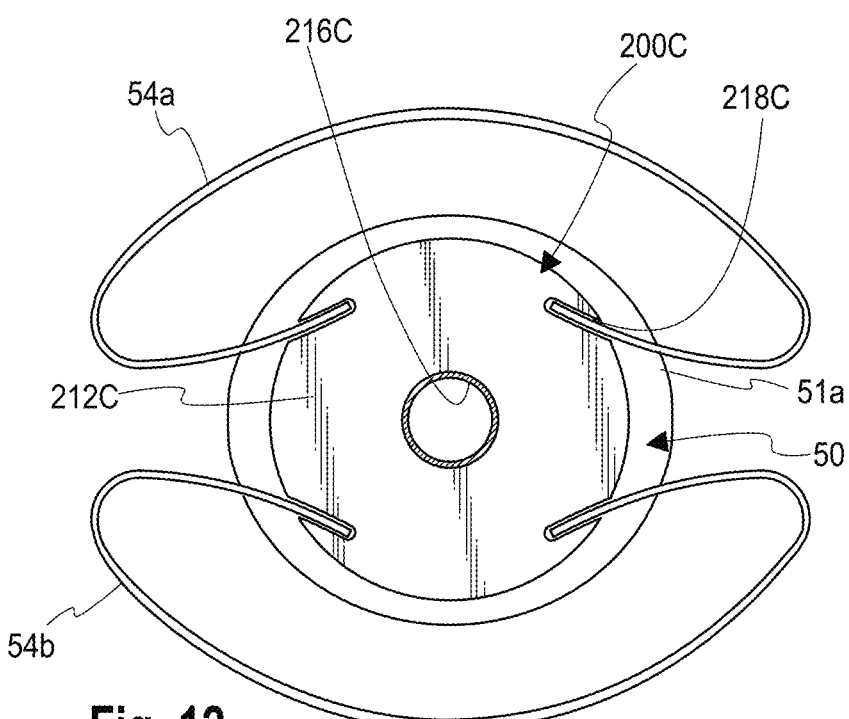
FIG. 12 illustrates a top plan view of another embodiment of a lens mate shown implanted over an intraocular lens.

With reference now to FIG. 12, a lens mate 200C may be provided with a lens body 212C, aperture 212C, and a plurality of U-shaped cutouts or channels 218C in the periphery of the body 212C that capture or mechanically engage the haptics of the primary IOL, such as the haptics 54a/54b of the aforementioned IOL 50 as illustrated. The engagement of the lens mate 200C with the primary IOL prevents substantial relative motion between the two bodies when implanted in the eye as shown in FIG. 12.

It will be understood that the laser or irradiation-based techniques described above for modification of the refractive index of the mate 200 may be suitably used for the other embodiments of the mate 200A, 200B, 200C described and/or illustrated.

The invention claimed is:

1. An apparatus for implantation in an eye, the apparatus comprising:
 a lens body for providing vision correction for a patient, said lens body having an initial index of refraction,
 wherein said lens body is formed from at least one material configured to have a second index of refraction when subjected to a laser and/or radiation, said lens body having a central aperture, said lens body having at least one zone surrounding said central aperture having an index of refraction that is different from that of a remaining portion of said lens body.

2. The apparatus of claim 1 wherein said lens body is a flat disc.

3. The apparatus of claim 1 wherein said lens body is formed from a transparent material and said central aperture includes a darkened perimeter.

4. The apparatus of claim 1 wherein said central aperture has the form of an elongate slot.

5. The apparatus of claim 1 wherein said central aperture is a circular hole.

6. The apparatus of claim 1 further comprising a pair of haptics extending from said lens body.

7. The apparatus of claim 1 further comprising at least one peripheral slot on a peripheral portion of said lens body for engaging a haptic of another IOL.

8. The apparatus of claim 1 in combination with an IOL and arranged such that said apparatus overlies and is anterior of said IOL when implanted in the eye.

9. The apparatus of claim 1 wherein said lens body is formed from a photosensitive material.

10. The apparatus of claim 1 wherein said lens body includes a layer of a photosensitizer.

11. The apparatus of claim 1, wherein a first portion of said lens body is formed from a first polymer and a second portion of said lens body is formed from a second polymer, said second polymer being softer than said first polymer.

12. The apparatus of claim 1, wherein said lens body is formed from at least one material configured to have a second index of refraction when subjected to a femtosecond laser.

13. A method of implanting the apparatus of claim 1 in an eye, the method comprising the steps of:
 obtaining the apparatus of claim 1;
 implanting said apparatus in the eye; and
 applying a femtosecond laser to said central lens body to change said initial index of refraction with said apparatus in situ.

* * * * *